(12) United States Patent
Nomikou (10) Patent No.: US 11,040,101 B2
(45) Date of Patent: Jun. 22, 2021

(54) NANOPARTICLES FOR CANCER THERAPY AND DIAGNOSIS

(71) Applicant: UCL BUSINESS PLC, London (GB)

(72) Inventor: Nikolitsa Nomikou, New Barnet (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 16/385,591

(22) Filed: Apr. 16, 2019

(65) Prior Publication Data

US 2020/0330598 A1 Oct. 22, 2020

(51) Int. Cl.
| | |
|---|---|
| A61K 38/00 | (2006.01) |
| A61K 41/00 | (2020.01) |
| A61K 9/00 | (2006.01) |
| A61K 9/51 | (2006.01) |
| A61P 35/00 | (2006.01) |

(52) U.S. Cl.
CPC ........ *A61K 41/0071* (2013.01); *A61K 9/0019* (2013.01); *A61K 9/5146* (2013.01); *A61K 9/5192* (2013.01); *A61K 41/0033* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 9,919,059 B2 | 3/2018 | Wong et al. | |
| 2007/0237827 A1 | 10/2007 | Sung et al. | |
| 2008/0194653 A1* | 8/2008 | Murakata | A61K 31/433 514/361 |
| 2013/0028932 A1 | 1/2013 | Borrebaeck et al. | |

OTHER PUBLICATIONS

Khalil et al. (Int. J Mol Sci. Feb. 2017; 18(2): 313).*
Vlakh et al. (Polymers, 2016, vol. 8, 212).*
Wu et al. (ACS Appl. Mater. Interfaces 2017, 9, 14596-14605).*
Calixto et al., "Nanotechnology-Based Drug Delivery Systems for Photodynamic Therapy of Cancer: A Review," Molecules 21(3): 342 (2016).
Hadi et al.,"Multistimulus-responsive nanoparticles for optimising sonodynamic therapy in prostate cancer," Abstract from 3rd ASPIC International Congress meeting, Lisbon, Portugal (Oct. 5, 2018 to Nov. 5, 2018).
Nagavarma et al.,"Different techniques for preparation of polymeric nanoparticles—a review," Asian J. Pharm. Clin. Res, 5(3): 16-23 (2012).
Nomikou et al., "A versatile, stimulus-responsive nanoparticle-based platform for use in both sonodynamic and photodynamic cancer therapy," Acta Biomaterialia, 49: 414-421 (2017).
Tarassoli et al., "Cathepsin B-degradable, NIR-responsive nanoparticulate platform for target-specific cancer therapy," Nanotechnology, 28(5): 055101 (2016).
Wang et al., "Indocyanine green-incorporating nanoparticles for cancer theranostics," Theranostics, 8(5): 1227 (2018).
Zhu et al., "Nanoenzyme-augmented cancer sonodynamic therapy by catalytic tumor oxygenation" Acs Nano 12(4): 3780-3795 (2018).
Zhu et al., "Self-Assembling Stereocomplex Nanoparticles by Enantiomeric Poly (γ-glutamic acid)-poly (lactide) Graft Copolymers as a Protein Delivery Carrier," Macromolecular Bioscience, 14(4): 576-587 (2014).
Nomikou, "A novel tumour-responsive formulation for delivering sonodynamic treatment of prostate cancer," Grant proposal/Abstract, UK Research and Innovation (2018).

* cited by examiner

*Primary Examiner* — Jeanette M Lieb
(74) *Attorney, Agent, or Firm* — Nixon Peabody LLP; David S. Resnick; Ravinderjit Braich (57) ABSTRACT

The present invention relates generally to methods and materials for use in photothermal or sonodynamic therapy. The invention novel nanoparticles for use in delivering sensitizers to solid tumour target, wherein the nanoparticles are composed of a polymers or co-polymer of monomers linked by peptide bonds, wherein the polymer or co-polymer comprises one or both of glutamate or derivatised glutatamic acid, and optionally a further, different, monomer which is a naturally occurring amino acid or synthetic monomer having a side chain group, wherein the polymer or co-polymer is not composed only of glutamate. The pendant groups and/or side chains of the polymer or co-polymer interact non-covalently with the sensitizer.

18 Claims, 7 Drawing Sheets
(7 of 7 Drawing Sheet(s) Filed in Color)

NANOPARTICLES FOR CANCER THERAPY AND DIAGNOSIS

FIELD OF THE INVENTION

The present invention relates generally to methods and materials for use in photothermal or sonodynamic therapy.

BACKGROUND OF THE INVENTION

The poor prognosis in many types of cancers, such as pancreatic and advanced prostate cancer, is mainly due to late diagnosis, with a large proportion of patients having metastatic disease at presentation. Chemotherapy has been the golden standard for managing unresectable disease and for downstaging. However, this approach is associated with systemic toxicity and severe side effects, including impairment of the immune system which contributes to further tumour progression. Importantly, evidence has immerged reporting the development of cancer resistance to even the most advanced and potent chemotherapeutic agents, leading to more aggressive and unmanageable disease after a certain period of drug exposure. Tumour heterogeneity is another important issue that has rendered chemotherapy inadequate and inefficient as a treatment approach.

During the last decades, there is very little improvement in terms of prognosis for certain cancer types, such as pancreatic and advanced prostate cancer. This accentuates the necessity for the development of alternative treatments that can supplement chemotherapy and radiotherapy or they can be applied as stand-alone first-line treatments for unresectable disease. Almost two decades ago, patients with advanced pancreatic cancer were treated with percutaneous interstitial photodynamic therapy (PDT) as an alternative treatment modality. The outcomes were encouraging in terms of safety of the approach and prognosis improvement. However, the application of PDT for pancreatic cancer treatment is associated with major limitations, including the invasive mode of treatment that does not allow frequent application, as well as the poor penetration of light through tissue that limits its efficacy and confines the ablation only around the fibre optic tip.

The mechanism of PDT is discussed, for example by Calixto et al. (Nanotechnology-Based Drug Delivery Systems for Photodynamic Therapy of Cancer: A Review. *Molecules* 2016, 21, 342)

Over the past decade, efforts to evaluate and optimize therapeutic modalities, based on low-intensity ultrasound (sonodynamic therapy) and near-infrared light (NIR/photothermal ablation) for cancer treatment, have radically increased.

Sonodynamic therapy (SDT) employs low intensity ultrasound in combination with sensitizing agents, such as porphyrins, for the production of cytotoxic free radicals and the subsequent ablation of tumours.

In a similar manner, NIR/photothermal therapy employs NIR light, in combination with sensitizing agents that absorb in the NIR region of the electromagnetic spectrum, for the confined ablation of tumours based on both the hyperthermic effect at the microscopic level and the production of free radicals.

In clinical studies to establish the antitumour effect of ultrasound and NIR light in the presence of relatively non-toxic sensitizers, the sensitizers have typically been administered as free agents. Due to their low solubility and bioavailability this approach results in limited tumour accumulation of the agent with subsequent reduced treatment efficacy.

Optimisation of these energy-based tumour ablation approaches using nanotechnology has been suggested to improve their therapeutic potential in the clinic. This is due to the improved tumour accumulation of the sensitising agent, when delivered in the form of nanoparticles which can carry hydrophobic sensitizers through the blood circulation.

However good sensitizer loading, as well as the ability to deliver the sensitizer at the site of action, are critical properties of a nanoparticle based system.

The tumour microenvironment contains upregulated proteolytic enzymes required for cancer progression. These endogenous tumour-specific characteristics provide valuable tools for the design of formulations with enhanced activity in the tumour microenvironment. Polyglutamate (PGA) is among the biodegradable polymeric molecules that have been successfully used in drug delivery systems for cancer, mainly as PGA-drug conjugates. PGA can be digested by cathepsin-B, which is a lysosomal protease in normal cells and tissues. In malignant tumours, the expression of cathepsin-B is highly upregulated and the enzyme is secreted into the extracellular environment.

PGA has also been suggested to be used as adjuvant material, for effective anti-tumour immune response, which plays an important role in the successful eradication of tumours. This is potentially beneficial since conventional treatments, such as chemotherapy and surgery, are associated with immunosuppressive effects. Moreover, common hyperthermic ablation techniques fail to preserve tumour antigens intact in order to raise anti-tumour immune response.

U.S. Pat. No. 9,919,059 relates to a multistage nanoparticle drug delivery system for the treatment of solid tumours, in which graft copolymers comprising a polymeric backbone comprising a poly(amino acid), such as poly(Glu), are used to deliver therapeutic drugs as polymer drug conjugates.

U.S. 20130028932A1 relates to pharmaceutical compositions comprising an immunostimulatory polypeptide and polyglutamic acid nanoparticles, formulated in a pharmaceutically acceptable diluent, carrier or excipient. Such compositions are reported to have utility in stimulating the immune system in subjects U.S. 20070237827A1 relates to nanoparticles composed of chitosan, poly-glutamic acid, and at least one bioactive agent of HMG-CoA reductase inhibitors or erythropoietin. The nanoparticles are reported to have a positive surface charge and enhanced permeability for paracellular drug delivery.

Tarassoli et al. described a nanoparticulate formulation that is based on polyglutamate that carries the photothermal and sensitising agent indocyanine green. (Tarassoli S, Martinez de Pinillos S, Pye H, Mosse C A, Callan J F, Macrobert S, McHale A P, Nomikou N†. Cathepsin B-degradable, NIR-responsive nanoparticulate platform for target-specific cancer therapy. Nanotechnology (Gold open access) 2017; 28:055101)

Sensitizer-carrying nanoparticles based on different types of biodegradable polymers, such as poly(lactic-co-glycolic acid), have also been developed (Nomikou, N., et al. "A versatile, stimulus-responsive nanoparticle-based platform for use in both sonodynamic and photodynamic cancer therapy." *Acta biomaterialia* 49 (2017): 414-421). Although, these formulations have shown to improve intratumoural uptake, they are not responsive exclusively to the tumour microenvironment, in terms of enzymatic digestion.

Polymeric and lipid-based nanoparticles carrying the photothermal agent and sensitizer ICG have also been developed in the past (Wang, Haolu, et al. "Indocyanine green-incorporating nanoparticles for cancer theranostics." Theranostics 8.5 (2018): 1227). However, similarly, those formulations did not respond to the tumour microenvironment for increasing cellular uptake or for recovering quenched fluorescence.

Zhu et al. "Nanoenzyme-Augmented Cancer Sonodynamic Therapy by Catalytic Tumour Oxygenation." ACS nano 12.4 (2018): 3780-3795, describes the use of multifunctional nanosonosensitizers constructed by the integration of a MnOx component with biocompatible/biodegradable hollow mesoporous organosilica nanoparticles, followed by conjugation with protoporphyrin (as a sonosensitizer) and cyclic arginine-glycine-aspartic pentapeptide (as a targeting peptide).

Thus it can be seen that novel nanoparticle system for delivering and dispersing sensitizing molecules for the purpose of ultrasound- and/or light-mediated tumour ablation and imaging would provide a contribution to the art.

Prior to the present application an abstract entitled "A novel tumour-responsive formulation for delivering sonodynamic treatment of prostate cancer" was made available on the UK Research and Innovation website:
https://gtr.ukri.org/projects?ref=EP % 2FP020828%2F1

This also discusses the use of sensitizer-containing polyglutamate based nanoparticles for use in SDT.

The following oral presentations originating from the present inventor have also been given before the present filing date:

"Exploiting the tumour microenvironment in order to optimise sonodynamic therapy for prostate cancer". Authors: Mohammad Hadi N, Andini Palilu D, Ahmed H, Callan J, Macrobert A, McHale A, Nomikou N. Presented at the International Conference on tumour Microenvironment, Lisbon, Portugal, Jun. 10-14, 2018.

"Multistimulus—responsive nanoparticles for optimising sonodynamic therapy in prostate cancer". Authors: Mohammad Hadi N, Andini Palilu D, Ahmed H, Callan J, Macrobert A, McHale A, Nomikou N. Presented at the 3$^{rd}$ ASPIC International Congress, Lisbon, Portugal, May 10-11, 2018.

SUMMARY OF THE INVENTION

The present invention is based on the use of nanoparticles formed by specific polyglutamate-based polymers or co-polymers or derivatives thereof. These nanoparticles contain and bind non-covalently to sensitizing molecules, such porphyrins. The nanoparticles can improve the performance of these sensitizers in ultrasound- and/or light-mediated tumour ablation and imaging.

As explained above, polyglutamic acid (PGA) as a carrier for therapeutic agents (e.g. paclitaxel, ICG, etc.) has previously been suggested. However the present inventor has demonstrated that the PGA polymer forms nanoparticles with relatively poor sensitizer loading efficiency.

Figure 3:
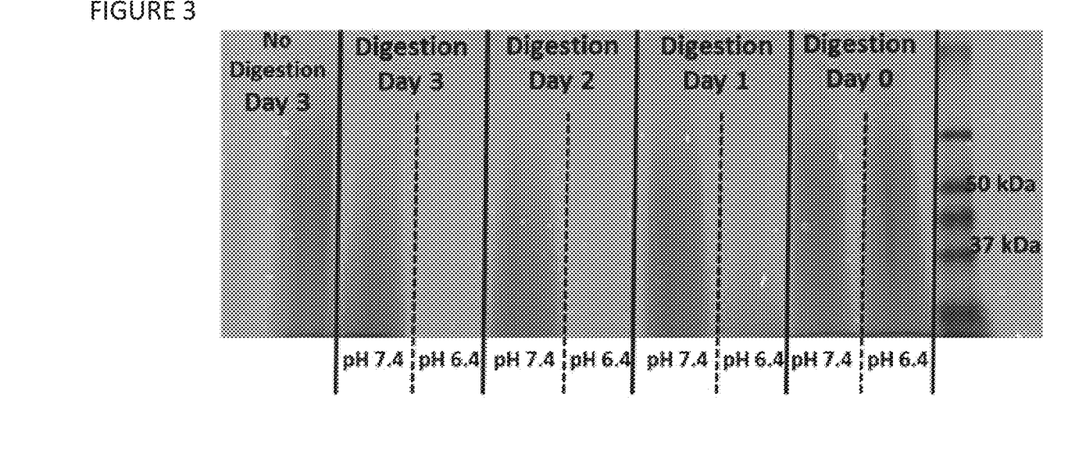
FIG. 3: SDS-PAGE for PGATyr digested by cathepsin B at 370 C over 3 days. Digestion by cathepsin B at acidic pH is characteristic of the tumour environment.

By contrast, the nanoparticulate system of the invention is based on sensitizer-containing nanostructures of PGA-based polymers and co-polymers and derivatives, so which are not solely composed of glutamate. As demonstrated herein, such formulations are self-assembling, can be effectively loaded with sensitizer, but can nevertheless still be digested by cathepsin-B (FIG. 3) and other proteases associated with the low pH tumour microenvironment, leading to a decrease in nanoparticle size and subsequent increased cellular uptake. Thus, in addition to providing the known benefits of PGA-per se based approaches, the use of the present invention can unexpectedly improve delivery and distribution of the sensitizer throughout the tumour mass leading to better therapeutic outcomes.

Figure 1:
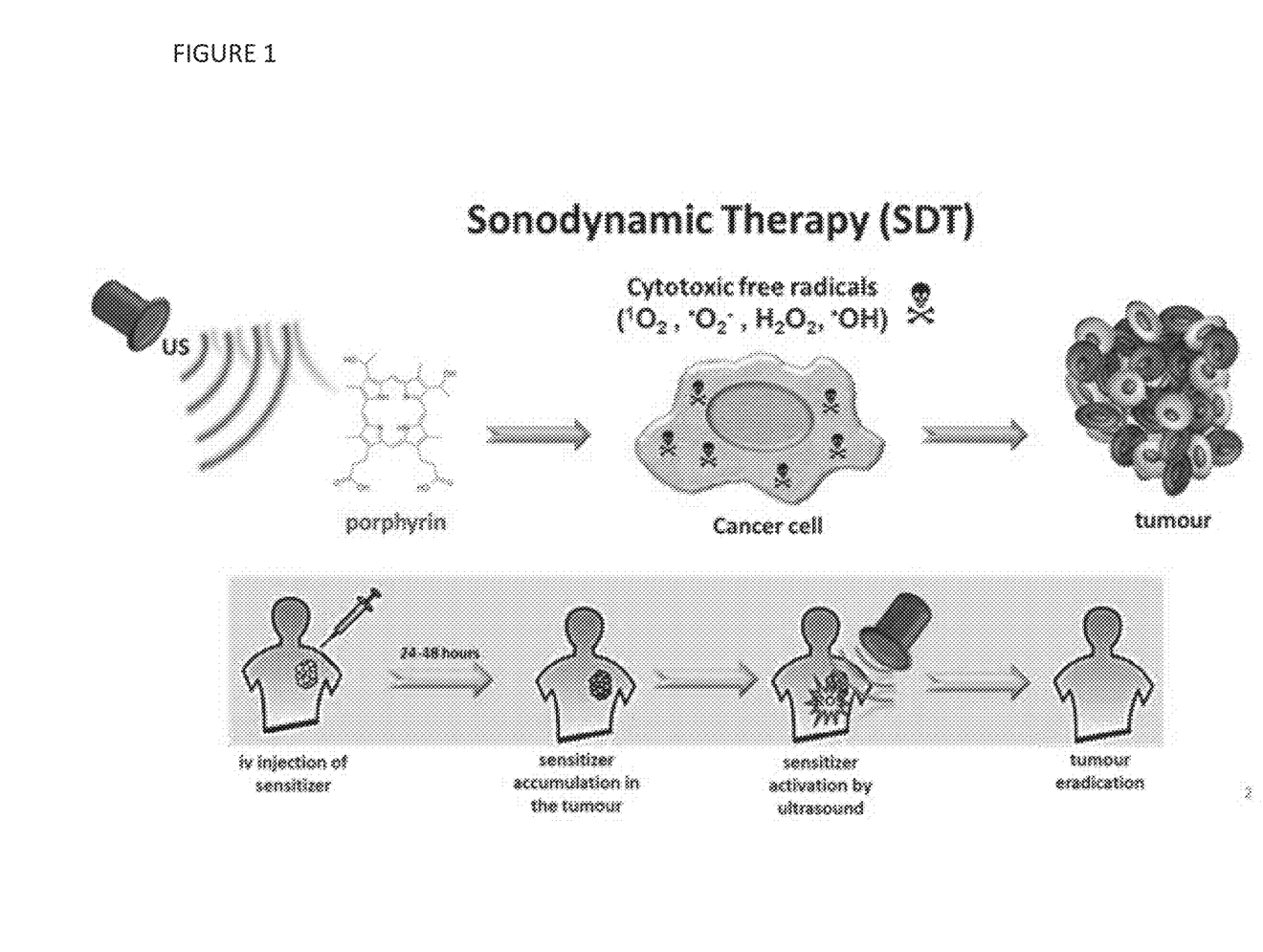
FIG. 1: A schematic illustration of the mechanism and effect of SDT.
Figure 2:
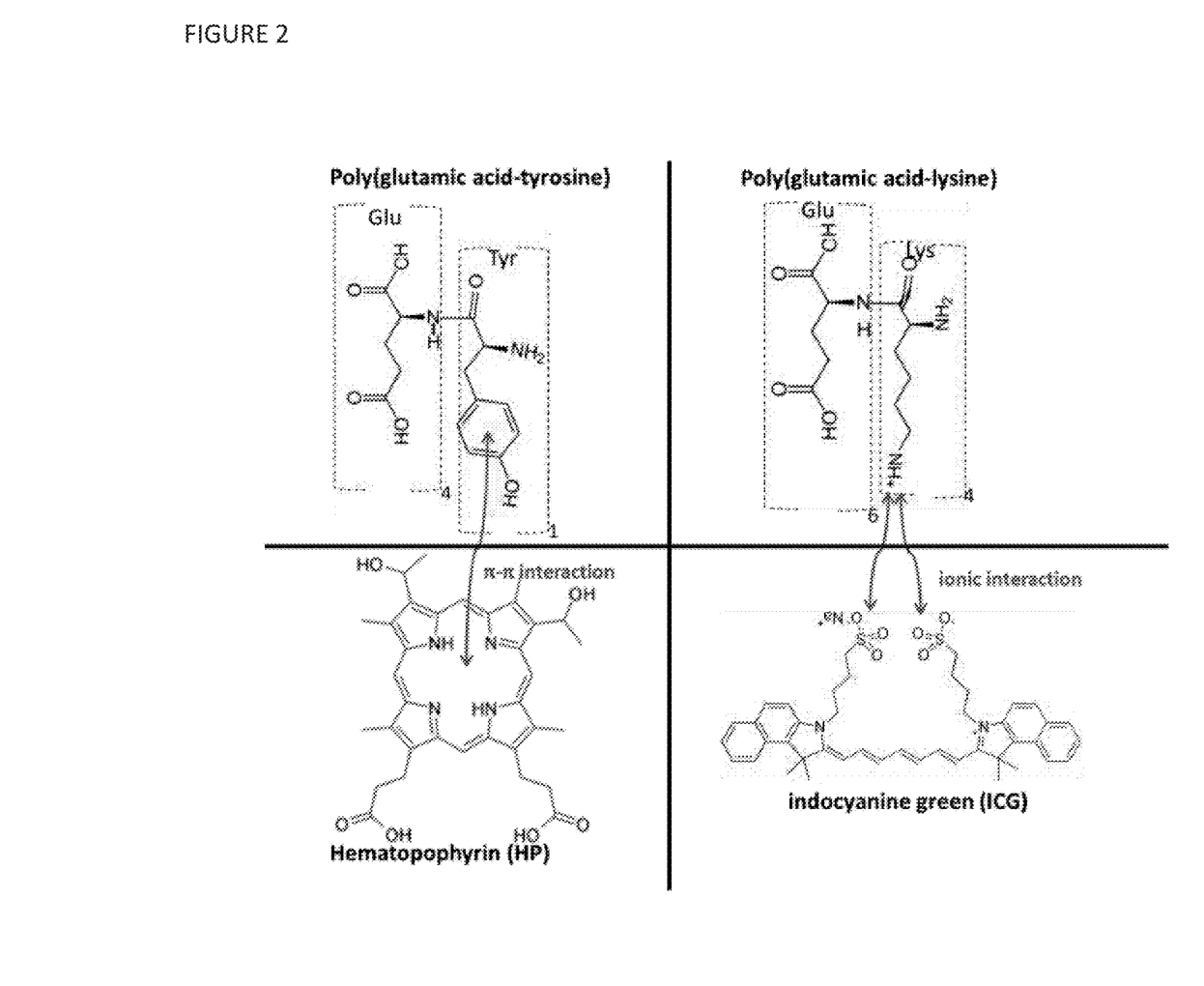
FIG. 2: Examples of potential interactions between the PGA-based co-polymers and sensitizing agents

Furthermore, the nanoparticles of the present invention do not require covalent attachment of the payload (FIG. 2). Such chemical/covalent conjugation of molecules is known to lower their cytotoxic activity (Orbán E, Mezo G, Schlage P, Csik G, Kulić Z, Ansorge P, Fellinger E, Möller H M, Manea M. In vitro degradation and antitumour activity of oxime bond-linked daunorubicin-GnRH-III bioconjugates and DNA-binding properties of daunorubicin-amino acid metabolites. Amino Acids. 2011 July; 41(2):469-83. doi: 10.1007/s00726-010-0766-1. Epub 2010 Oct. 16)

The nanoparticles described herein not only show significantly improved sensitizer loading efficiency, but are sensitive to and compatible with internal tumour stimuli such as cathespin-B and other overexpressed tumour enzymes, low pH, hypoxia, and other properties of the tumour microenvironment. Using these nanoparticles, the sensitizer can be efficiently taken up and distributed intratumorally, throughout the dense tumour mass. Furthermore, the components of the formulation are non-toxic and the production process is compatible with GMP requirements. The product can be conveniently provided as a lyophilised powder which can be reconstituted and mixed at the point of care.

The combination of properties provided by the present nanoparticle makes them extremely versatile in SDT and NIR based therapies.

In the case of formulations containing the NIR-emitting sensitizer (such as ICG or other dyes) the fluorescence of the sensitizer is quenched while it is in the form of intact nanoparticles. However, as shown in the Examples below NIR fluorescence is recovered upon digestion with cathepsin-B.

This recovery of fluorescence under the conditions mimicking those of the tumour microenvironment has significant potential in NIR imaging for the accurate intraoperative delineation of tumours or the detection of residual undetected microscopic disease, post-surgical resection.

In summary, the multistimulus-responsive anticancer nano-formulations of the present invention provide for increased tumour accumulation of the sensitizer, improved distribution throughout the tumour mass, as well as enhanced cellular uptake at the site of the tumour. These effects can improve the efficacy of SDT and NIR/photothermal treatment, and may result in more efficient confined tumour ablation, including the ablation of cancer that surrounds vascular structures, and reduction in off-target effect.

The invention also provides for imaging or theranostic utilities when suitable sensitizers are used.

Thus in one aspect there is provided a nanoparticle for use in delivering a sensitizer to a solid tumour target,
wherein exposure of said sensitizer to either NIR or ultrasound causes ablation of said tumour,
wherein the nanoparticle is composed of a polymer or co-polymer of monomers linked by peptide bonds,
wherein the polymer or co-polymer comprises one or both of monomers M1 and M2,
wherein M1 is glutamate,
wherein M2 is glutamic acid wherein a carboxyl group is derivatised with a pendant group,
wherein the pendant group is selected from: a lipid; a group comprising an aromatic ring; a positively-charged group; an aliphatic group;

wherein the polymer or co-polymer optionally further comprises monomer M3 which is different to M1 and M2, wherein M3 is either a naturally occurring amino acid having a side chain group, or M3 is a synthetic monomer having a side chain group wherein the side chain group is selected from: a positively charged group; a polar uncharged group; a hydrophobic group, wherein the polymer or co-polymer comprises at least M2 or M3, and whereby the pendant groups and/or side chains of the polymer or co-polymer bind or interact non-covalently with the sensitizer.

"Nanoparticle", as used herein, generally refers to a particle of any shape having a diameter from about 1 nm up to, but not including, about 1 micron, preferably from 3 nm to about 200 nm, more preferably from 10 to 100 nm, more preferably from 15 to 40, 60, 80, or 100 nm.

The size of nanoparticles can be experimentally determined using a variety of methods known in the art, including transmission electron microscopy (TEM), scanning electron microscopy, dynamic light scattering (DLS), gel filtration chromatography (GFC), and fluorescence correlation spectroscopy (FCS). In the Examples herein, DLS was utilised.

As explained below, the mean radius of the nanoparticles will decrease following protease digestion.

"Mean radius" or "mean diameter" as used herein, generally refers to the statistical mean particle size of the nanoparticles in a population of undigested nanoparticles. The "diameter" of an essentially spherical nanoparticle may refer to the physical or hydrodynamic diameter. The diameter of a non-spherical nanoparticle may refer preferentially to the hydrodynamic diameter. As used herein, the diameter of a non-spherical nanoparticle may refer to the largest linear distance between two points on the surface of the nanoparticle. Mean particle size can be measured using methods known in the art, such as dynamic light scattering. "Radius" is to be interpreted likewise as half the diameter.

The peptide bonds ensure the nanoparticle is capable of being hydrolysed by a protease. Preferably, the nanoparticle is susceptible to proteolysis by cathepsin-B, leading to a decrease in nanoparticle size and subsequent increased cellular uptake by the tumour.

The nanoparticle may be a co-polymer of M1 and M3, not comprising M2.

In co-polymers the Glu will preferably be in excess over the amino acid or other monomer, since a high proportion of Glu is advantageous in maintaining targeted enzymatic digestion at the site of action.

In the present invention the PGA may be a co-polymer with an amino acid, preferably a naturally occurring amino acid.

Thus in one embodiment M3 may be a proteinogenic amino acid with a side chain.

The side chain group may optionally be selected from: a positively charged group; a polar uncharged group; a hydrophobic group (e.g. an aromatic ring); an aliphatic group.

Preferred amino acids are those with positively charged side chains (lysine, arginine, histidine), with polar uncharged side chains (asparagine and glutamine) for establishing hydrogen bond-based interactions with sensitizers, or with hydrophobic side chains (tyrosine, tryptophan, phenylalanine, methionine, leucine, isoleucine).

Other amino acids with negative charged side chains may optionally be desirable in conjunction with positively-charged sensitizers.

Preferably M3 is selected from lysine, arginine, histidine, asparagine and glutamine, tyrosine, tryptophan, phenylalanine, methionine, leucine, and isoleucine, more preferably selected from, tyrosine and lysine. An example is the co-polymer is Glu/Tyr or Glu/Lys.

Optionally the co-polymer is Glu/Tyr in the ratio 4:1.

Optionally the co-polymer is Glu/Lys in the ratio 6:4.

Where ratios are stated, preferably they are provided as contiguous sequences: for example 6:4 is provided as 6Glu then 4Lys repeating.

As used herein "hydrophobic" groups are those which have a greater affinity for, and thus solubility in, organic solvents as compared to water. The hydrophobicity of a compound (and hence group) can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the organic solvent than in the water, then the compound is considered hydrophobic.

The nanoparticle may be a polymer of M1 and M2, not comprising M3.

In one embodiment herein the free carboxyl group is derivatised with a pendant group which is lipid.

Thus example derivatives of PGA for use in the present invention are PGA-lipid polymers in which a percentage of carboxylic acid groups of the poly-L-glutamic acid (PGA) side chains are derivatised with lipid molecules.

Preferred lipids are glycerolipids such as triacylglycerides or phospholipids such as glycerophospholipid, phosphatidylcholine, phosphatidylethanolamine or phosphatidylserine Preferred Examples include 1,2-dihexanoyl-sn-glycero-3-phosphoethanolamine and 1,2-Dioleoyl-sn-glycero-3-phosphoethanolamine. Preferably, the fatty acids are selected from $C_{5-20}$alkyl and $C_{5-20}$alkenyl.

As demonstrated herein this can increase loading efficiency. Without wishing to be bound by theory it is understood that this improvement may be supported by two mechanisms:

Firstly, via increased interaction with aliphatic chain: Some sensitizers, such as indocyanine green, are amphiphilic and can intercalate into the double aliphatic chain of lipid molecules. Other sensitizers, such as hematoporphyrin, are hydrophobic and may strongly interact with the lipid aliphatic chains through hydrophobic interactions.

Secondly, via PGA structural folding: Incorporation of lipid molecules in PGA can increase structural folding of the polymer in aqueous media resulting in more stable nanoparticles (in the absence of proteolytic enzymes) and hence higher sensitizer loading efficiency.

In addition to increasing loading efficiency, the incorporation of lipid molecules in the PGA chain can improve the fluorescence emission properties of indocyanine green (Kraft, John C., and Rodney J Y Ho. "Interactions of indocyanine green and lipid in enhancing near-infrared fluorescence properties: the basis for near-infrared imaging in vivo." Biochemistry 53.8 (2014): 1275-1283).

In one embodiment herein the free carboxyl group is derivatised with a pendant group which is a positively charged group; a polar uncharged group; a hydrophobic group (e.g. an aromatic ring); an aliphatic group.

In one aspect there is provided a nanoparticle for use in delivering a sensitizer to a solid tumour target, wherein exposure of said sensitizer to either NIR or ultrasound causes ablation of said tumour,
wherein the nanoparticle is composed of a polymer or co-polymer of monomers linked by peptide bonds, wherein the polymer or co-polymer comprises one or both of monomers M1 and M2, wherein each of monomers M1 and M2 is of formula (I) or (II) wherein the bonds shown outside of the square brackets represent continuation of the polymeric chain, or termini:

(I)

(II)

wherein in M1, Z is —OH,
wherein in M2, Z is $Q^A$;
wherein $Q^A$ is a pendant group selected from: a lipid; a group comprising an aromatic ring; a positively-charged group; an aliphatic group
and wherein M3 is of formula (III);

(III)

wherein q and r are 0 or 1;
wherein $X^A$, $X^B$, $X^C$, $X^D$, $X^E$, and $X^F$ are selected from H or $Q^B$;
wherein at least one of $X^A$, $X^B$, $X^C$, $X^D$, $X^E$, and $X^F$ is $Q^B$;
wherein $Q^B$ is a side chain group is selected from: a positively charged group; a polar uncharged group; a hydrophobic group.

In some embodiments q is 1 and r is 0; preferably q and r are 0. Preferably only one of $X^A$, $X^B$, $X^C$, $X^D$, $X^E$, and $X^F$ is $Q^B$;

In one embodiment $Q^A$ is a pendant group which is a lipid.
In one embodiment $Q^B$ is the sidechain of a naturally occurring amino acid.

In other embodiments $Q^B$ may be e.g. $C_{6-10}$carboaryl, $C_{5-9}$heteroaryl, $C_{3-10}$alkyl, $C_{3-10}$alkenyl, $C_{3-10}$alkynyl, $C_{3-8}$cycloalkyl, $C_{3-8}$heterocycloalkyl, $C_{1-4}$alkyl$C_{6-10}$carboaryl, $C_{1-4}$alkyl$C_{5-9}$heteroaryl, $C_{1-4}$alkyl$C_{3-8}$cycloalkyl and $C_{1-4}$alkyl$C_{3-8}$heterocycloalkyl;
wherein said carboaryl, heteroaryl, alkyl, alkenyl, alkynyl, cycloalkyl and
heterocycloalkyl can be optionally substituted with one or more halo, cyano, $OR^a$,
$NR^aR^b$, oxo, sulfonyl, sulfinyl, sulfanyl, sulfonamido, carbamido;

wherein $R^a$ and $R^b$ are independently selected from H or $C_{1-6}$alkyl.

Thus the invention provides:

Clause [1] A nanoparticle for use in delivering a sensitizer to a solid tumour target,
wherein exposure of said sensitizer to either NIR or ultrasound causes ablation of said tumour,
wherein the nanoparticle is composed of a polymer or co-polymer of monomers linked by peptide bonds, wherein the polymer or co-polymer comprises one or both of monomers M1 and M2,
wherein M1 is glutamate,
wherein M2 is glutatamic acid wherein a carboxyl group is derivatised with a pendant group,
wherein the pendant group is selected from: a lipid; a group comprising an aromatic ring; a positively-charged group; an aliphatic group;
wherein the polymer or co-polymer optionally further comprises monomer M3 which is different to M1 and M2,
wherein M3 is either a naturally occurring amino acid having a side chain group,
or M3 is a synthetic monomer having a side chain group
wherein the side chain group is selected from: a positively charged group; a polar uncharged group; a hydrophobic group,
wherein the polymer or co-polymer comprises at least M2 or M3, and
whereby the pendant groups and/or side chains of the polymer or co-polymer interact non-covalently with the sensitizer.

Clause [2] A nanoparticle according to Clause [1] further encapsulating said sensitizer, which is non-covalently bound to the pendant groups and/or side chains of the polymer or co-polymer.

Clause [3] A nanoparticle according to any one of Clause [1] to Clause [2], which is a co-polymer of M1 and M3.

Clause [4] A nanoparticle according to any one of Clause [1] to Clause [3], wherein M3 is selected from lysine, arginine, histidine, asparagine and glutamine, tyrosine, tryptophan, phenylalanine, methionine, leucine, and isoleucine, more preferably selected from, tyrosine and lysine.

Clause [5] A nanoparticle according to Clause [4] wherein the co-polymer is Glu/Tyr or Glu/Lys.

Clause [6] A nanoparticle according to any one of Clause [1] to Clause [2], which is a polymer of M1 and M2.

Clause [7] A nanoparticle according to any one of Clause [1] to Clause [6], wherein the carboxyl group is derivatised with a pendant group which is lipid.

Clause [8] A nanoparticle according to any one of Clause [1] to Clause [7], wherein each of monomers M1 and M2 is of formula (I) or (II), (I)

-continued (II)

wherein in M1, Z is —OH,
wherein in M2, Z is $Q^A$;
wherein $Q^A$ is a pendant group selected from: a lipid; a group comprising an aromatic ring; a positively-charged group; an aliphatic group
and wherein M3 is of formula (III);

(III)

wherein q and r are 0 or 1;
wherein $X^A$, $X^B$, $X^C$, $X^D$, $X^E$, and $X^F$ are selected from H or $Q^B$;
wherein at least one of $X^A$, $X^B$, $X^C$, $X^D$, $X^E$, and $X^F$ is $Q^B$;
wherein $Q^B$ is a side chain group is selected from: a positively charged group; a polar uncharged group; a hydrophobic group.

Clause [9] A nanoparticle according to Clause [8] wherein q and r are 0 and/or only one of $X^A$, $X^B$, $X^C$, $X^D$, $X^E$, and $X^F$ is $Q^B$.

Clause [10] A nanoparticle according to Clause [8] wherein $Q^A$ is a pendant group which is a lipid and/or $Q^B$ is the sidechain of a naturally occurring amino acid.

Clause [11] A nanoparticle according to any one of Clause [1] to Clause [10] comprising equal to or at least 30-6,000 monomers.

Clause [12] A nanoparticle according to any one of Clause [1] to Clause [11] having a mass of 5-500 kDa; 10-200 kDa; 20-150 kDa or 20-100 kDa; 20-50 kDa or 50-100 kDa.

Clause [13] A nanoparticle according to any one of Clause [1] to Clause [12] wherein the sensitizer is selected from the list consisting of: porphyrins, chlorins, and phthallocyanines, and is optionally hematoporphyrin.

Clause [14] A nanoparticle according to any one of Clause [1] to Clause [12] wherein the sensitizer is a cyanine dye, and is optionally ICG.

Clause [15] A process for preparing a nanoparticle according to any one of Clause [1] to Clause [14], which process comprises:
(a) providing the polymer or copolymer;
(b) optionally derivatising the free carboxyl group of the glutamate with the pendant group;
(c) preparing nanoparticles by sonication of the polymer or copolymer in a solvent in the presence of the sensitizer;
(d) optionally lyophilising the nanoparticles.

Clause [16] A method of treating a solid tumour, the method comprising administering to a subject a nanoparticle encapsulating a sensitizer according to any one of Clause [1] to Clause [14] such as to deliver said sensitizer to the tumour, and exposing said sensitizer to either NIR or ultrasound to cause ablation of said tumour.

Clause [17] A method according to Clause [16], wherein the nanoparticle is administered by intravenous injection or infusion, optionally into the tumour or vicinity of the tumour.

Clause [18] A method according to Clause [16] or Clause [17], wherein the solid tumour is selected from the group consisting of adenocarcinomas, carcinomas, hemangiomas, liposarcomas, lymphomas, melanomas, and sarcomas.

Clause [19] A method according to any one of Clause [16] to Clause [18], wherein the treatment is for prostate cancer or for pancreatic cancer.

Clause [20] A method according to any one of Clause [16] to Clause [19], wherein the NIR or ultrasound is locally applied to the vicinity of the tumour.

Clause [21] A method according to any one of Clause [16] to Clause [20], wherein the treatment is used in combination with chemotherapy and/or radiotherapy Clause [22] A method of imaging a solid tumour in a subject, the method comprising administering to the subject a nanoparticle encapsulating a sensitizer according to any one of Clause [1] to Clause [14] wherein the sensitizer fluoresces upon irradiation with NIR, wherein in the presence of the tumour the nanoparticle is digested by a tumour associated protease thereby enhancing the fluorescence on application of NIR.

Clause [23] A method according to Clause [22] wherein the protease is cathepsin-B or prostate-specific membrane antigen.

Clause [24] A method according to Clause [22] or Clause [23] wherein the imaging is for the accurate intraoperative delineation of tumour or the detection of residual undetected disease, post-surgical resection.

Clause [25] A tumour theranostic method comprising performing the method of any one of Clause [16] to Clause [21] in combination with the method of any one of Clause [22] to Clause [24] in the subject.

Clause [26] Use of a nanoparticle encapsulating a sensitizer according to any one of Clause [1] to Clause [14] for NIR or ultrasound therapy, imaging, or theranostics, optionally as defined in a method of any one of Clause [16] to Clause [24].

Clause [27] A nanoparticle encapsulating a sensitizer according to any one of Clause [1] to Clause [14] for use in NIR or ultrasound therapy, imaging, or theranostics, optionally as defined in a method of any one of Clause [16] to Clause [24].

Clause [28] Use of a nanoparticle encapsulating a sensitizer according to any one of Clause [1] to Clause [14] in the preparation of medicament for NIR or ultrasound therapy, imaging, or theranostics, optionally as defined in a method of any one of Clause [16] to Clause [24].

BRIEF DESCRIPTION OF THE DRAWINGS

This patent or application file contains at least one drawing executed in color. Copies of this patent or patent application publication with color drawing (s) will be provided by the Office upon request and payment of the necessary fee.

DETAILED DESCRIPTION OF THE INVENTION

As explained above, PGA based polymers have been used previously in nanoparticles, although not in the context of the present invention. For example Zhu et al. (2014) describe nanoparticulate formulations that is based on poly-glutamate-based a co-polymers that carry proteins, as distinct from sensitizing agents (Zhu Y, Akagi T, Akashi M. Self-assembling stereocomplex nanoparticles by enantiomeric poly(γ-glutamic acid)-poly(lactide) graft copolymers as a protein delivery carrier. Macromol Biosci. 2014 Apr. 14(4):576-87).

Furthermore PGA salts, and derivatives and co-polymers thereof, can be obtained commercially in various molecular weights (for example from Sigma-Aldrich/Merck as "POLY-L-GLUTAMIC ACID", or "Poly-L-γ-glutamic acid sodium salt"), or prepared as described in the Examples herein. Monomer Glu residues (or derivatives thereof) within PGA can be polymerised via the gamma- or alpha-carboxyl groups.

Typically, to prepare the nanoparticles of the invention, PGA polymer or co-polymer is provided. This can be derivatised (optionally after blocking the terminal amine group) using methods known in the art. Thus in addition to the synthetic methodologies discussed herein, alternative reactions and strategies useful for the preparation of the derivatised polymers and co-polymers disclosed herein are known in the art. See, for example, March, "Advanced Organic Chemistry," 5$^{th}$ Edition, 2001, Wiley-Interscience Publication, New York).

Nanoparticles comprising the PGA polymer of co-polymer (optionally derivatised) and encompassing sensitizer can also be prepared using conventional methods for forming nanoparticles. For example by use of poly-vinyl alcohol (PVA) and sonication, followed by dialysis using a suitable molecular weight cut off dialysis material, and ultrafiltration (again using a suitable molecular weight cut off). Other methods of preparing nanoparticles are known in the art—see e.g. Nagavarma, B. V. N., et al. "Different techniques for preparation of polymeric nanoparticles—a review." Asian J. Pharm. Clin. Res 5.3 (2012): 16-23.

Preferred polymers are in the mass range 5-500 kDa e.g. 10-200 kDa, e.g. 20-150 kDa, e.g. 20-100 kDa, e.g. 50-100 KDa or 20-50 kDa. Preferred polymers include will include 30 to 6000 monomer units.

Thus in one aspect there is provided a process for preparing a nanoparticle of the invention, which process comprises:

(a) providing the glutamate containing polymer or copolymer;

(b) optionally derivatising the free carboxyl group of the glutamate with the pendant group;

(c) preparing nanoparticles by sonication of the polymer or copolymer in a solvent in the presence of the sensitizer;

Optionally the sensitizer containing nanoparticles are freeze dried for storage before use.

In one aspect the invention provides such a process substantially as described herein, with reference to the Description and Figures.

Sensitizers

The sensitizer or sensitizing agent employed in the present invention will be appropriate to the therapeutic or diagnostic modality.

For example for SDT the sensitizing agent will generate cytotoxic free radicals when exposed to ultrasound.

For NIR (including other photothermal) the sensitizing agent will absorb in the NIR region of the electromagnetic spectrum leading to highly localised increased temperature (hyperthermic effect) and the production of free radicals.

Suitable sensitizers for both these interventions are known to those skilled in the art.

For SDT the sensitizer is used for the production of cytotoxic free radicals and the subsequent ablation of tumours.

Examples include porphyrins, which are macrocyclic compounds with bridges of one carbon atom joining pyrroles to form a characteristic tetrapyrrole ring structure. There are many different classes of porphyrin derivatives (such as hematoporphyrin, photofrin, tetraphenylporphyrins, etc.). Other example SDT compounds include chlorins (such as HPPH, foscan, verteporfin, chlorin(e6), etc.), phthallocyanines (such as silicon phthalocyanine (PC4), RLP068, etc.)

A preferred sensitizer for the present invention is a hematoporphyrin.

Near-infrared (NIR) fluorescence imaging agents typically have high extinction coefficients, large Stokes' shifts, and the ability to generate strong fluorescence emission at the range of 700 to 1000 nm (see e.g. Shi, Changhong, Jason B. Wu, and Dongfeng Pan. "Review on near-infrared heptamethine cyanine dyes as theranostic agents for tumour imaging, targeting, and photodynamic therapy." Journal of Biomedical Optics 21.5 (2016): 050901). Examples include cynanine dyes and other commercially available NIRF dyes e.g. Cy5.5, IRDye800-CW, Indocyanine green (ICG). Examples of heterocyclic polymethine cyanines with dual imaging and targeting properties include IR-780, IR-783, IR-808, and MHI-148.

A preferred sensitizer for the present invention is a ICG.

Sensitizing agents that operate in the NIR region of the electromagnetic spectrum have particular utility for the confined ablation of tumours based on both the hyperthermic effect at the microscopic level and the production of free radicals The loading of number of sensitizers in the nanoparticle can be varied in view of a range of factors, including the identity of the sensitizer, the tumour to be treated, and the overall design of the therapeutic regimen. However, as explained above, a higher loading is generally advantageous.

In some of these embodiments, the loading of the nanoparticle is about 20% to about 100% by weight, more preferably at least 70%, 80%, 90% or 95% by weight. Loading may be assessed using standard methods in the art e.g. spectrophotometry (absorbance and fluorescence), based on a standard curve for each sensitizer Therapeutic and Diagnostic Utilities Extensive preclinical experimentation has demonstrated the advantages of SDT and NIR/photothermal therapy are targeted, minimally-invasive treatment modalities, particularly over photodynamic therapy and systemic chemotherapy. They do not require the administration of highly toxic agents; thus, accumulation of these agents in off-target organs, up to reasonable levels, is not an issue. Therefore, they are not associated with adverse side effects and they can be applied repeatedly. Further highlighting their benefits, no cancer cell population has shown resistance to therapy-triggered ROS production with simultaneous inhibition of ROS "neutralization", thus far. This is particularly important, considering the issue of multidrug resistance development using even the most advanced anticancer agents. It is also of high importance because it has a vast potential to address the issue of tumour heterogeneity that has rendered current treatments for advanced tumours inadequate. Moreover, one of the major advantages of non-hyperthermic ablation therapies, including SDT, is their immunogenicity, i.e. they leave tumour-associated antigens intact, subsequently inducing anti-tumour immune response against the primary or locally recurrent and disseminated disease.

Also provided by the present invention are methods of treatment, diagnosis, and theragnosis utilising the nanoparticles of the invention. In particular, there are methods provided of treating patients by NIR/photothermal therapy, or SDT for the ablation of a tumour in patient using said nanoparticles.

Typically, the nanoparticle is used in an effective amount. An "effective amount", as used herein, is an amount being fit for the purpose intended. Thus for diagnostics this will be sufficient to generate a signal. For therapy and theranostics this will be sufficient to show benefit to the individual, optionally in combination with other therapies as described herein. The actual amount administered, and rate and time-course of administration, will depend on the subject and the intervention in hand. Decisions on dosage etc. are within the responsibility of general practitioners and other medical doctors, and will typically take account of the purpose of the imaging and\or disorder to be treated, the condition of the individual patient, the site of delivery, the method of administration and other factors known to practitioners.

Thus the invention provides a method of treating a solid tumour comprising administering to a subject a nanoparticle encapsulating a sensitizer as described herein to deliver said sensitizer to the tumour, and exposing said sensitizer to either NIR or ultrasound to cause ablation of said tumour.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress (prolonged survival), a halt in the rate of progress, regression of the condition, amelioration of the condition, and cure of the condition.

In the present invention treatment may be e.g. for the purpose of slowing tumour growth, halting tumour growth, or decreasing tumour size.

Typically, the nanoparticle is administered by intravenous injection or infusion, systemically or, optionally, into the tumour or vicinity of the tumour, and the NIR or ultrasound is locally applied to the vicinity of the tumour. In the case of ultrasound, an appropriate "acoustic window" through which ultrasound can be transmitted is used to irradiate the target tumour. These treatments can also be applied intra-operatively (during surgical procedure), to eliminate residual disease after surgical resection or to irradiate the tumour bed and eliminate undetected residual microscopic disease post-surgical resection. Clinical-grade lasers for NIR treatment are commercially available e.g. from BIOMED 25 (Biomed Ltd, UK).

Commercially available ultrasound systems for clinical SDT include those available from Intelect Transport Ultrasound by Chattanooga Medical Supply Inc., USA. Typically commercial systems capable of producing ultrasound at 0.5-5 MHz frequency and 0.5-10 W/cm$^2$ power density range are suitable for use in the present invention.

The treatment may be used in combination with chemotherapy and/or radiotherapy

As explained above, for SDT the sensitizer is used for the production of cytotoxic free radicals. When the system is used with SDT, the site-specific application, minimally invasive, of low-intensity ultrasound may be used to further induce agent dispersion through dense and poorly-diffused tumours (Nomikou et al (2010) "Ultrasound-enhanced drug dispersion through solid tumours and its possible role in aiding ultrasound-targeted cancer chemotherapy." Cancer Lett 288(1): 94-98).

Thus, the nanoparticles described herein may thus be used to produce reactive oxygen species to selected cells (such as tumour cells) in vivo.

Sensitizing agents that absorb in the NIR region are used to provide a localised hyperthermic effect and for the production of free radicals upon irradiation with NIR light.

Thus, the nanoparticles described herein may thus be used to produce a localised hyperthermic effect to selected cells (such as tumour cells) in vivo.

The nanoparticles described herein may be used as adjuvant material in relation to an effective anti-tumour immune response, since they are not immunosuppressive, can preserve tumour antigens, and may have antitumour immuno-adjuvant properties(Seth A, et al. Infection-mimicking poly (γ-glutamic acid) as adjuvant material for effective anti-tumor immune response. Int J Biol Macromol. 2015 April; 75:495-504).

The tumour may be a solid tumour, by which is meant an abnormal mass of tissue that results from the uncontrolled proliferation of cells. Typically, solid tumours do not contain cysts or liquid areas within the tissue mass. Solid tumours can arise in any part of the body, and may be benign (not cancerous) or malignant (cancerous). Most types of cancer other than leukemias can form solid tumours. Solid tumours include, for example, adenocarcinomas, carcinomas, hemangiomas, liposarcomas, lymphomas, melanomas and sarcomas.

As explained herein the tumour microenvironment has certain characteristics such as a "leaky" vasculature and poor lymphatic drainage, high collagen concentration and Interstitial Fluid Pressure, increased concentration of proteolytic enzymes such as cathepsin B, acidic pH, and hypoxia.

The tumour microenvironment also provides an enhanced permeability and retention (EPR) effect, and the overexpression of particular cell membrane receptors. Among these, the EPR effect involves atypical and leaky vasculature, as well as poor lymphatic drainage that promote nanoparticle accumulation and retention in tumours (*Nomikou N, Curtis K, McEwan C, Callan B, Callan J F, McHale A P. A versatile, stimulus-responsive nanoparticle-based platform for use in both sonodynamic and photodynamic cancer therapy. Acta Biomaterialia 2017; 49: 414-421)

Optionally the nanoparticles may have a mean average diameter larger than the average diameter of the vasculature of the normal tissue and smaller than the diameter of the tumour vasculature.

The size of nanoparticles of the invention decreases in the presence of cathepsin B thereby facilitating uptake of the nanoparticles and sensitizer, as well as adequate diffusion throughout a dense tumour mass. Thus cellular uptake of the nanoparticles is proportional to the intracellular and secreted levels of cathepsin B.

Prostate cancer is the second most common cancer and the sixth leading cause of cancer death among men worldwide, with an estimated recorded amount of 1.1 million cases and 377,000 deaths in 2017, which accounts for 15% of all new cases of cancer in men Its incidence is set to increase with advancing age demographics in developing countries. Once the cancer has spread beyond the prostate, it becomes relatively unmanageable. The only available strategy to reduce progression-related toxicity and premature death is early detection combined with well-tolerated interventions. Current treatments leave much to be desired. In the recent quality of life report from the PROTECT study, half the men exhibited urinary incontinence at one year and two thirds reported significant sexual function impairment following surgical intervention. Focal therapy has resulted in a much better toxicity profile than standard-of-care treatments, but the interventions have proved resistant to widespread diffusion as they are difficult to perform.

The nanoparticles of the invention are degraded by prostate-specific membrane antigen (PSMA) which has glutamate carboxypeptidase activity (see Chang, Sam S. "Overview of prostate-specific membrane antigen." Reviews in urology 6.Suppl 10 (2004): S13).

The nanoparticles can offer improved sensitizer (e.g. hematoporphyrin) diffusion and distribution throughout the dense and poorly-vascularised mass of prostate tumours, with a subsequent potential to improve the efficacy of SDT. They can optionally be used in conjunction with transrectal ultrasound.

As explained above in the case of formulations containing an NIR-absorbing sensitizer (such as ICG or other dye) the fluorescence of the sensitizer is quenched while it is in the form of intact nanoparticles. However, as shown in the Examples below NIR fluorescence is recovered upon digestion with cathepsin-B.

This recovery of fluorescence under the conditions mimicking those of the tumour microenvironment has significant potential in NIR imaging for the accurate intraoperative delineation of tumours or the detection of residual undetected microscopic disease, post-surgical resection.

Thus there is also provided a method of imaging a solid tumour in a subject, the method comprising administering to the subject a nanoparticle encapsulating a sensitizer according to the invention wherein the sensitizer fluoresces in the presence of NIR, wherein in the presence of the tumour the nanoparticle is hydrolysed by a tumour associated protease thereby enhancing the fluorescence on application of NIR.

As explained above, the protease may (for example) be cathepsin-B or prostate-specific membrane antigen.

Kits

In another aspect the present invention provides kits comprising a nanoparticle as described herein, optionally with instructions for use for performing a method of treatment, diagnosis, or a theranostic method as described herein. Optionally the kit may also include a source of NIR or ultrasound.

Wherever a composition (e.g. of nanoparticles) is described herein, it will be appreciated that the same composition for use in the therapeutic methods (including theranostic and diagnostic methods) described herein is also envisaged, as is the composition for use in the manufacture of a medicament for treating or imaging the relevant disease.

Likewise where a method utilising nanoparticles is described, it will be appreciated that use of a nanoparticle encapsulating a sensitizer in that method, a nanoparticle encapsulating a sensitizer for use in that method, and use of a nanoparticle encapsulating a sensitizer in the preparation of medicament for that method is also envisaged.

Thus the invention further provides:
Use of a nanoparticle encapsulating a sensitizer of the invention for NIR or ultrasound therapy, imaging, or theranostics;
A nanoparticle encapsulating a sensitizer of the invention for use in NIR or ultrasound therapy, imaging, or theranostics;
Use of a nanoparticle encapsulating a sensitizer of the invention in the preparation of medicament for NIR or ultrasound therapy, imaging, or theranostics.

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

EXAMPLES

Example 1—Derivatisation with Lipid 1,2-Dioleoyl-sn-glycero-3-phosphoethanolamine, for ICG-carrying Nanoparticles with Applications in Near-infrared Imaging Method Blockage of amine terminal groups of PGA: 10 mg PGA salt (MW: 50-100 kDa) were dissolved in 2 mL of 0.1M sodium phosphate buffer (pH 7.3). 2.5 mg of Sulfo-NHS acetate were dissolved in 200 uL 0.1M sodium phosphate buffer and this was added to the PGA solution, under constant stirring. The reaction was allowed to run under stirring at room temperature for 1 hr. The solution was dialysed for 24 hrs against de-ionised water and then freeze-dried for 24 hrs.

Carboxyl group substitution (1:50) with lipid molecule: 3 mg sulfo-NHS and 4 mg EDC were dissolved in 5 mL PGA 2 mg/mL solution in water. The resulting solution was heated at 80° C. in a sonicating bath and a 5 mL 1,2-Dioleoyl-sn-glycero-3-phosphoethanolamine 140 µg/mL solution in water (also at 80° C.) was added drop-wise. The reaction was allowed to take place at 70° C. for 3 hrs. The product was dialysed against water for 12 hrs and the derivative was freeze-dried for 24 hrs.

Nanoparticle fabrication: 10 mg of the lipid-derivatised PGA sodium salt (MW: 50-100 kDa) and 5 mg of ICG were dissolved in 10 mL DMSO. This solution was then added drop-wise to a 5 mL poly-vinyl alcohol (PVA, MW: 85-124 kDa) solution under constant bath sonication. The resultant mixture was dialysed (MWCO: 8 kDa) against deionised water for 12 h (overnight). The mixture was then probe-sonicated for 3 mins and subjected to 4 rounds of ultrafiltration (MWCO: 100 kDa, 1 round=1000 RPM for 15 mins). The suspension retained by the filter was ultracentrifuged at 38,000 g for 90 min at 12° C. The precipitated pellet was suspended in 3 ml deionised water and probe-sonicated for 3 min to break down any aggregates. Second dialysis (MWCO: 8 kDa) was performed to remove any free ICG remaining, for 12 H. The solution was filter-sterilised using a micro-syringe filter and was snap-frozen followed by freeze-drying for 24 H. Lastly, the dry sample was suspended in 3 mL PBS and stored at 4° C., protected from light.

Result on loading efficiency: The derivatised formulation resulted in 34% loading efficiency for ICG, 4.25-fold higher than that achieved with original PGA (8% loading efficiency).

Example 2—Performance of the ICG-Carrying Nanoparticles Formed Using the Lipid-Derivatised PGA Method The ICG-carrying nanoparticles were prepared as described in example 1, using PGA that was derivatised with 1,2-dioleoyl-sn-glycero-3-phosphoethanolamine, by 1:50 substitution of PGA side-chain carboxyl groups (as described in Example 1)

Performance of Nanoparticles

Optical Properties of the ICG-carrying Nanoparticles Formed with the Lipid-derivatised PGA For time-depended fluorescence emission characterization, phosphate-buffered saline (PBS) solutions/suspensions containing free ICG, or ICG nanoparticles in the absence (ICGNP) or the presence (d.ICGNP) of cathepsin B (0.6 units/mL) were stored in an orbital incubator at 37° C., protected from light, for 2 days. The equivalent ICG concentration in all systems was 6 µg/mL. Fluorescence emission spectra of these systems were acquired over the course of 48 h. The excitation wavelength of 740 nm was used to obtain the fluorescence spectra. For the afore-mentioned experiments, spectra and fluorescence intensities were obtained using a CLARIOstar® High Performance Monochromator Multimode microplate reader (BMG LABTECH, UK).

Figure 4:
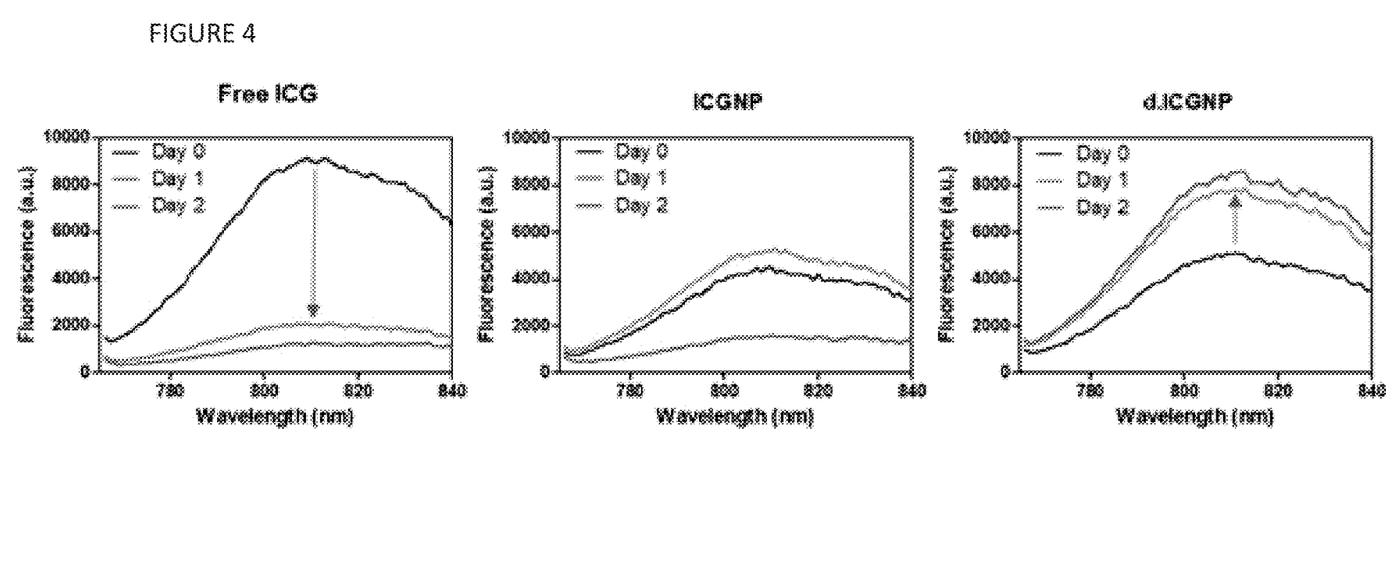
FIG. 4: Time-dependent evolution of the fluorescence spectra of free ICG (ICG), ICG-containing nanoparticles (ICGNP) and nanoparticles in the presence of cathepsin B (d.ICGNP), incubated at 37° C. in the time course of 2 days. The red arrow indicates the decrease or increase of ICG fluorescence after 24 h incubation.

The results shown in FIG. 4 demonstrate that incorporation of ICG in the nanoparticulate formulation results in significant suppression of fluorescence emission, which is recovered by 53% in 24 h and by 69% in 48 h, only in the presence of cathepsin B (FIG. 4). Fluorescence emission of free ICG was suppressed after 24 h.

The cathepsin B-induced increase in fluorescence emission observed at 24 h post-incubation of the nanoparticles demonstrate the utility of this formulation from a diagnostic perspective for the selective detection and imaging/delineation of highly aggressive tumours with elevated proteolytic enzyme activity.

Imaging

BxPC-3 (human pancreatic) cells were seeded with Corning Matrigel® Basement Membrane Matrix (VWR, UK) to a final concentration of $50 \times 10^3$ cells/well. After 24 h, the serum-containing growth medium was removed replaced with fresh serum-containing four different ICG systems: free ICG, ICG-containing nanoparticles (ICGNP), ICGNP with cathepsin B inhibitor (ICGNP+E-64) and ICGNP with cathepsin B (ICGNP+CB). The final concentrations in all systems was 15 µM in ICG, 0.6 units/mL in cathepsin B and 50 µM in E-64. Cells were incubated with these systems, protected from light, at 37° C. in a 5% CO2 humidified incubator for 24 hrs. The serum containing growth medium was then removed, and the cell matrices were washed twice with PBS. The plate was then incubated with PBS in the individual 3D culture-containing wells for 2 hrs. Before obtaining images with an NIR camera and starting the NIR-laserimaging and treatment, fresh serum-containing growth medium was added to individual cells.

Imaging was carried out under NIR laser excitation at 0.8 mW/cm$^2$ using a laser diode LDC 240 C (ThorLabs, UK), the systems are imaged using a NIR CCD camera C10600 ORCA-R2 (Hamamatsu, Japan) with a combination of filters: a 700 nm longpass filter, a 825 nm longpass filter and a 835 nm bandpass filter (Thorlabs, UK).

Figure 5:
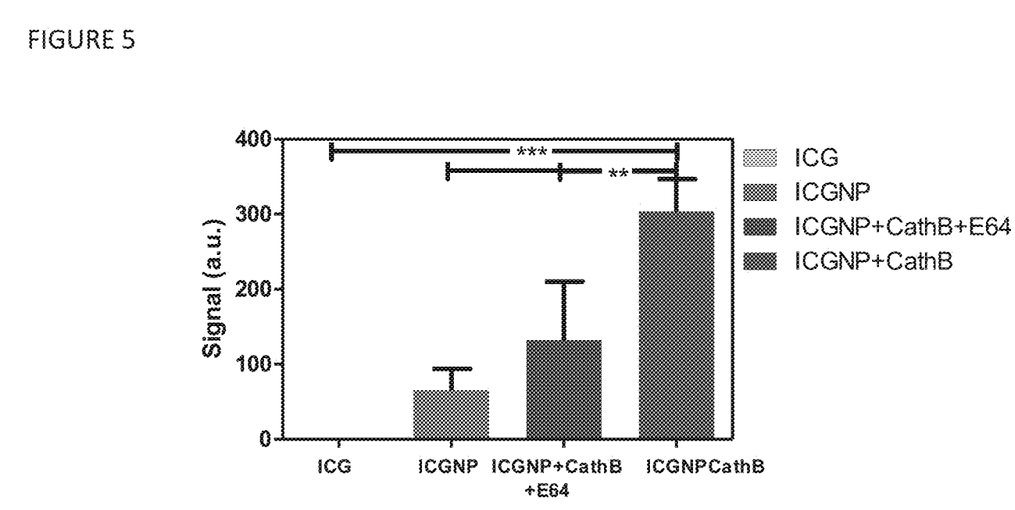
FIG. 5: Average signal obtained from NIR imaging of 3D matrices containing BxPC3 pancreatic cancer cell spheroids. Systems were incubated with free ICG (ICG), ICG-containing nanoparticles (ICGNP), ICGNP in the presence of cathepsin B and E-64, which is an inhibitor of cathepsin B, (ICGNP+CathB+E64) and ICGNP in the presence of cathepsin B (ICGNP+CathB). (n=3)

The results presented in FIG. 5 demonstrated the utility of the polyglutamate-based formulation in NIR imaging by verifying its efficacy to produce strong detectable signal after 24 h in cathepsin B-rich systems using pancreatic cancer cell-containing 3D matrices (FIG. 5).

These aptitudes demonstrate the potential of the formulation in intraoperative NIR treatment of residual microscopic disease or unresectable tumour segments.

Example 3—Co-Polymer of Poly Glutamic Acid with Tyrosine, for Hematoporphyrin (HP)-Carrying Nanoparticles with Applications in Sonodynamic Therapy Method 10 mg of either poly-l-glutamic acid sodium salt (PGA) (10 mg) (MW: 50-100 kDa) or poly-L-glutamic acid-tyrosine co-polymer 4:1 (PGATyr) (MW: 20-50 kDa) was mixed with 5 mg HP and dissolved in 10 mL DMSO. The resulting mixture was added drop-wise to a 5 mL polyvinyl alcohol solution (PVA, MW: 124 kDa) 0.5 mg/mL and the mixture was left under constant stirring for 1 hr. The mixture was then dialysed in membrane tubing (MWCO: 8 kDa) against water for 24 hr. Subsequently, the suspension was ultracentrifuged for 90 min at 38,000 g, at 12° C. The precipitated pellet was suspended in 3 mL deionised water and probe-sonicated for 3 min to break down any aggregates. Second dialysis was performed to remove any free HP remaining, for 12 hr. The solution was filter-sterilised using a 0.2 μm-pore filter and was snap-frozen followed by freeze-drying for 24 hrs. The dry sample was suspended in 3 mL PBS and stored at 4° C., protected from light.

For determining loading efficiency of the nanoparticles with hematoporphyrin (HP), a standard curve of the absorbance against HP concentration was used.

For cellular uptake studies, prostate cancer cells were seeded in wells of 96-well plates at a concentration of 2×10$^4$ cells/well and incubated for 24 hours. Cells were then treated with the following systems: Nanoparticles at 10 μg/mL based on HP, nanoparticles (10 μg/mL) with cathepsin B (10 units/mL), nanoparticles with E64, a cathepsin B inhibitor (1 mg/mL) and Free HP (10 μg/mL) at pH 7.4 in a hypoxic chamber (37° C., 1% Oxygen) and incubated for 48 hours. The formulation-containing medium was then removed, cell monolayers were washed with saline and fluorescence (excitation wavelength: 534 nm, emission wavelength: 626 nm) emission of the wells was measured using a microplate reader.

Figure 7:
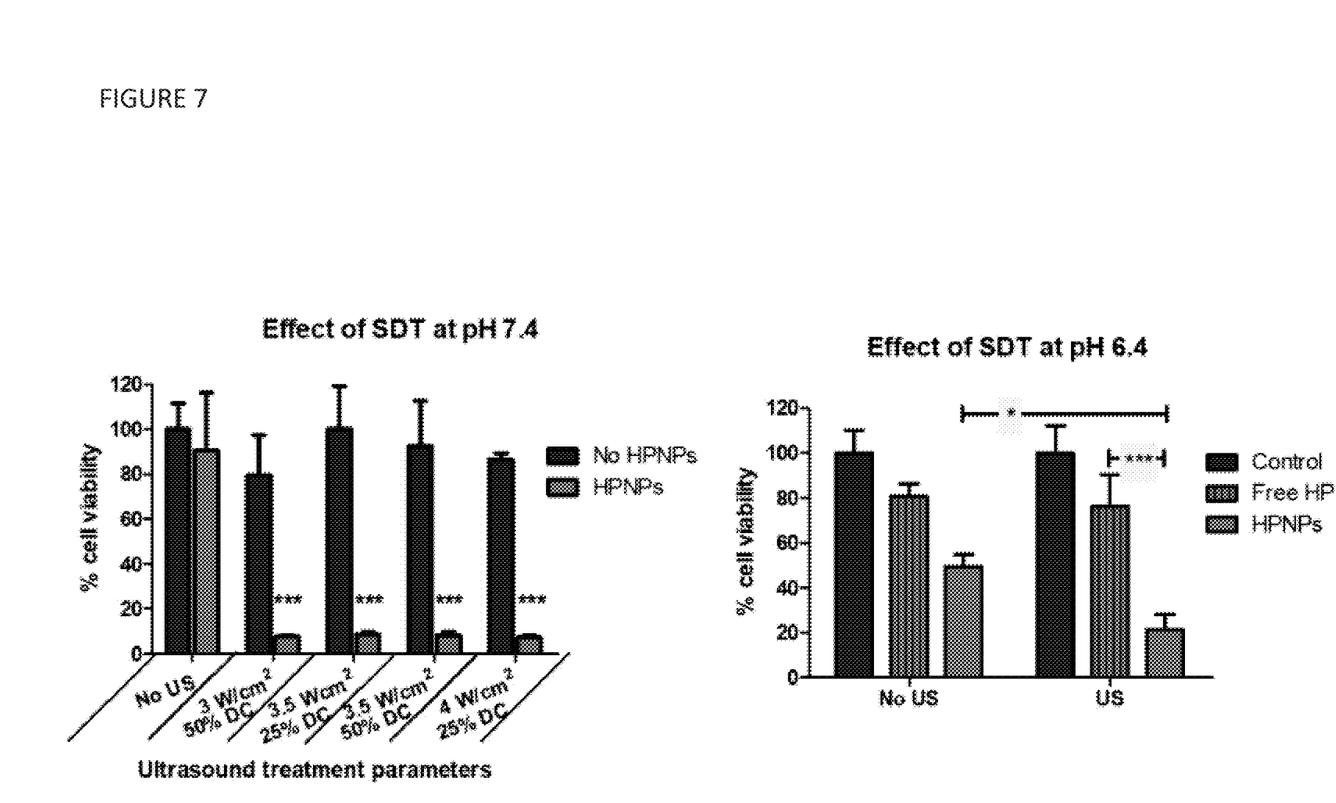
FIG. 7: Cell viability of LNCaP cells treated in the absence (No HPNPs) and the presence of nanoparticles (HPNPs), at 10 µg/mL HP concentration, without (No US) and with ultrasound exposure (30 sec) at different parameters and pH 7.4 (a.) and at 5 µg/mL HP, 3 W/cm$^2$, 50% DC at pH 6.4 (b.) (*$p<0.05$, ***$p<0.001$, n=4).

For the SDT efficacy studies, LNCaP cells were seeded in wells of 96-well plates (cell density: 10$^4$ cells/well) for 24 H. The systems were then incubated at either pH 7.4 or pH 6.4, in the presence or the absence of nanoparticles at 10 μg/mL or 5 μg/mL final HP concentration, respectively, in hypoxic environment. Cells were exposed to varying ultrasound conditions, as indicated in FIG. 7.

The in vivo studies were carried out in SCID mice bearing subcutaneous LNCaP tumours. The study was initiated when tumours reached 65-100 mm$^3$ volume. Mice were be treated with the formulation by tail-vein injection at nanoparticle concentration 6 mg/Kg based on HP. Ultrasound irradiation of the tumours, using a Sonidel SP100 sonoporator, was performed after 24 h (time-point of accumulation and confinement within the tumour mass, based on previous studies) and using ultrasound conditions optimised for in vivo SDT (3.5 W/cm$^2$, 30% Duty Cycle, for 3.5 min). Tumour volume was recorded using a Peira TM600 tumour-measuring device. The weight of mice was also recorded.

Result on loading efficiency: The preparation formed with the co-polymer of PGA and tyrosine resulted in 18% loading efficiency for HP, 3-fold higher than that achieved with original PGA (<3% loading efficiency), using this particular protocol.

Performance of Nanoparticles

Figure 6:
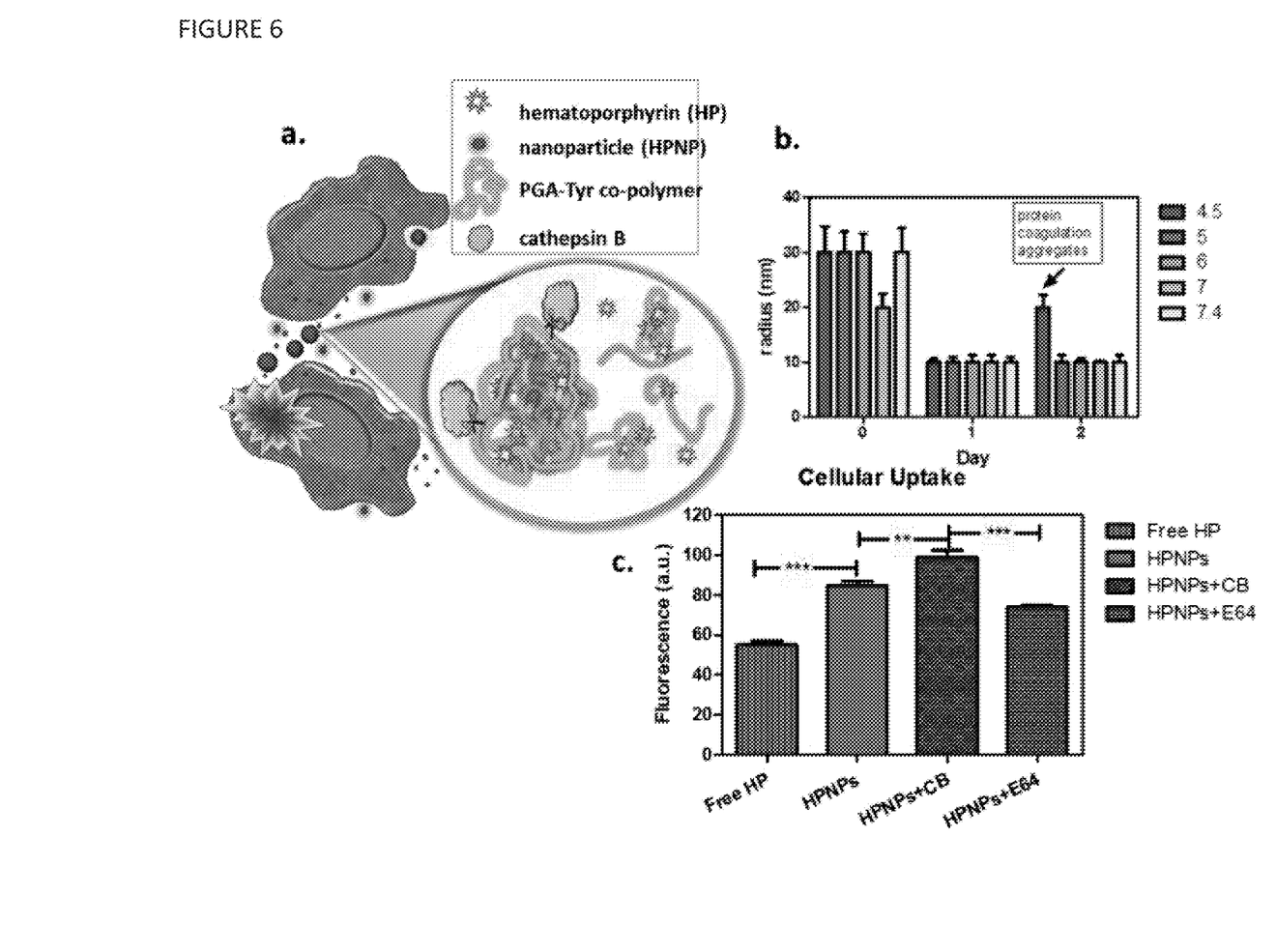
FIG. 6: a. Illustration of nanoparticle digestion in the tumour extracellular environment, b. Mean radius of the undigested (Day 0) and cathepsin B-digested hematoporphyrin-carrying PGATyr-nanoparticles, c. Cellular uptake of hematoporphyrin (HP) in systems incubated with free HP (HP), HP-containing PGATyr nanoparticles (HPNPs), HP-containing PGATyr nanoparticles with cathepsin-B (HPNPs+CB) and HP-containing PGATyr nanoparticles with cathepsin-B inhibitor (HPNPs+E64) (n=3).

Digestion of the formulation by cathepsin-B, at tumour-mimicking conditions (acidic pH), leads to decreased nanoparticle size and subsequent increased cellular uptake (FIGS. 6b and 6c, respectively).

Sonodynamic treatment, at both normoxic and hypoxic conditions, demonstrated ultrasound-induced cytotoxic effects only for the nanoparticle-treated prostate cancer cells, while toxicity of the formulation in the absence of ultrasound was minimal. We have also demonstrated significant cytotoxic effects of SDT under hypoxic conditions (FIG. 7), in which ROS production is expected to be limited.

Figure 8:
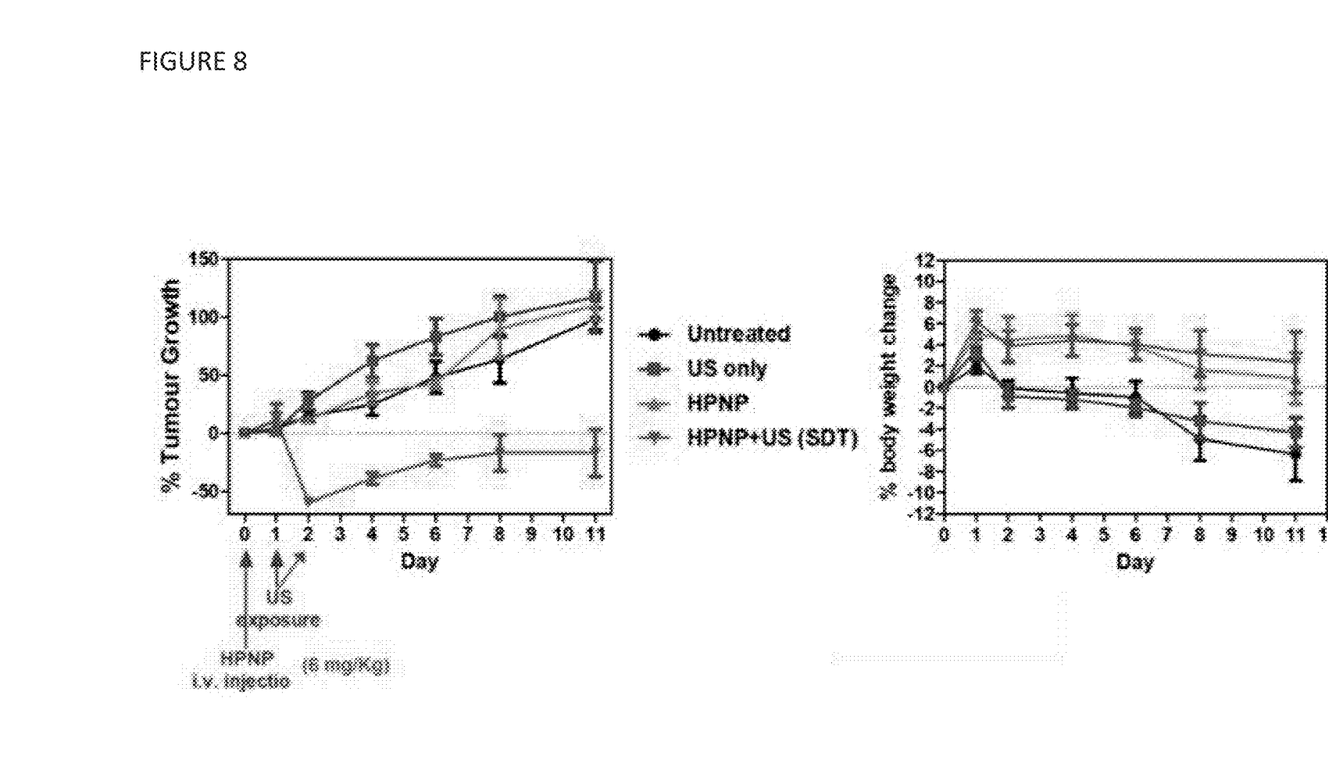
FIG. 8: Left hand side: Plot of % change in subcutaneous tumour volume for SCID mice treated with (i) no treatment (black) (ii) ultrasound only (blue) (iii) PGATyr-based nanoparticles carrying hematoporphyrin (green) and (iv) PGA-Tyr-based nanoparticles carrying hematoporphyrin with ultrasound (red). Animals were administered with the formulation on Day 0 and tumours were exposed to ultrasound (3 min) on Days 1 and 2. Right hand side: The corresponding body weight of animals. Error bars represent ± the standard error where n=4.

Our in vivo studies in immunodeficient mice, using the hematoporphyrin-containing PGATyr nanoparticles for SDT, showed a 60% decrease in LnCAP tumour volumes within 24 h, following IV administration of a single dose (FIG. 8, left hand side). No adverse effects were recorded and body weight was stable (FIG. 8, right hand side).

The invention claimed is:
1. A nanoparticle for use in delivering an amphiphilic or hydrophobic sensitizer to a solid tumour target,
   wherein exposure of said sensitizer to either NIR or ultrasound causes ablation of said tumor,
   wherein the nanoparticle contains, and binds non-covalently to, the sensitizer,
   wherein the nanoparticle is composed of a polymer or co-polymer of at least 30 monomers linked by peptide bonds, wherein the polymer or co-polymer comprises one or both of monomers M1 and M2,
   wherein M1 is glutamic acid,
   wherein M2 is glutamic acid wherein a carboxyl group is derivatised with a pendant group,
      wherein the pendant group is selected from: a lipid; a group comprising an aromatic ring; a positively-charged group; an aliphatic group;
   wherein the polymer or co-polymer optionally further comprises monomer M3 which is different to M1 and M2,
      wherein M3 is either a naturally occurring amino acid having a side-chain group,
      or M3 is a synthetic monomer having a side chain group
         wherein the side chain group is selected from: a positively charged group; a polar uncharged group; a hydrophobic group, wherein the polymer or co-polymer comprises at least M2 or M3, and whereby the pendant groups and/or side chains of the polymer of co-polymer interact non-covalently with the sensitizer.

2. A nanoparticle as claimed in claim 1 further encapsulating said sensitizer, which is non-covalently bound to the pendant groups and/or side chains of the polymer or co-polymer.

3. A nanoparticle as claimed in claim 1, which is a co-polymer of M1 and M3.

4. A nanoparticle as claimed in claim 1, wherein M3 is selected from lysine, arginine, histidine, asparagine and glutamine, tyrosine, tryptophan, phenylalanine, methionine, leucine, and isoleucine, more preferably selected from, tyrosine and lysine.

5. A nanoparticle as claimed in claim 4 wherein the co-polymer is Glu/Tyr or Glu/Lys.

6. A nanoparticle as claimed in claim 1, which is a polymer of M1 and M2.

7. A nanoparticle as claimed in claim 1, wherein the carboxyl group is derivatised with a pendant group which is lipid.

8. A nanoparticle as claimed in claim 1, wherein each of the monomers M1 and M2 is of formula (I) or (II), wherein in M1, Z is OH,
wherein in M2, Z is $Q^A$;
wherein $Q^A$ is a pendant group selected from: a lipid; a group comprising an aromatic ring; a positively-charged group; an aliphatic group
and wherein M3 is of formula (III);

wherein q and r are 0 or 1;
wherein $X^A$, $X^B$, $X^C$, $X^D$, $X^E$ and $X^F$ are selected from H or $Q^B$;
wherein at least one of $X^A$, $X^B$, $X^C$, $X^D$, $X^E$ and $X^F$ is $Q^B$;
wherein $Q^B$ is a side chain group selected from: a positively charged group; a polar uncharged group; a hydrophobic group.

9. A nanoparticle as claimed in claim 8 wherein q and r are 0 and/or only one of $X^A$, $X^B$, $X^C$, $X^D$, $X^E$ and $X^F$ is $Q^B$.

10. A nanoparticle is claimed in claim 8 wherein $Q^A$ is a pendant group which is a lipid and/or $Q^B$ is the sidechain of a naturally occurring amino acid.

11. A nanoparticle as claimed in claim 1 having a mass selected from the list consisting of: 5-500 kDa; 10-200 kDa, 20-150 kDa or 20-100 kDa; 20-50 kDa and 50-100 kDa.

12. A nanoparticle as claimed in claim 1, wherein the sensitizer is selected from the list consisting of: porphyrins, chlorins, phthallocyanines and cyanine dyes.

13. A process for preparing a nanoparticle as claimed in claim 1, which process comprises:

(a) providing the polymer or co-polymer;

(b) optionally derivatising the free carboxyl group of the glutamic acid with the pendant group;

(c) preparing nanoparticles by sonication of the polymer or co-polymer in a solvent in the presence of the sensitizer;

(d) optionally lyophylising the nanoparticles.

14. A method of treating a solid tumour, the method comprising administering to a subject a nanoparticle encapsulating a sensitizer according to claim 1 such as to deliver said sensitizer to the tumour, and exposing said sensitizer to either NIR or ultrasound to cause ablation of said tumor.

15. A method as claimed in claim 14, wherein the nanoparticle is administered by intravenous injection or infusion into the tumour or vicinity of the tumour and wherein ultrasound is locally applied to the vicinity of the tumour.

16. A method as claimed in claim 14, wherein the solid tumor is selected from the group consisting of adenocarcinomas, carcinomas, hemangiomas, liposarcomas, lymphomas, melanomas, and sarcomas.

17. A method as claimed in claim 14 which is a tumour theranostic method wherein the method of treating is performed in combination with a method of imaging the solid tumour in a subject, wherein the sensitizer fluoresces upon irradiation with NIR, and wherein in the presence of the tumour the nanoparticle is digested by a tumour associated protease, thereby enhancing the fluorescence on application of MR.

18. A method as claimed in claim 14 wherein the imaging is for the accurate intraoperative delineation of tumour or the detection of residual undetected disease, post-surgical resection.

* * * * *